(12) United States Patent
Mundell (10) Patent No.: US 8,487,610 B2
(45) Date of Patent: Jul. 16, 2013

(54) MAGNETISING ASSEMBLY

(75) Inventor: Paul Arthur Mundell, Cramlington (GB)

(73) Assignee: PII Limited, Cramlington, Northumberland (GB)

( * ) Notice: Subject to any disclaimer, the term of this patent is extended or adjusted under 35 U.S.C. 154(b) by 322 days.

(21) Appl. No.: 12/772,373

(22) Filed: May 3, 2010

(65) Prior Publication Data

US 2010/0283454 A1 Nov. 11, 2010

(30) Foreign Application Priority Data

May 7, 2009 (GB) .................................. 0907885.8

(51) Int. Cl.
*G01R 33/12* (2006.01)
(52) U.S. Cl.
USPC ............................ 324/220; 324/219; 324/221
(58) Field of Classification Search
USPC .................................................. 324/754, 220
See application file for complete search history.

(56) References Cited

U.S. PATENT DOCUMENTS

| | | | | |
|---|---|---|---|---|
| 3,483,466 | A * | 12/1969 | Beaver et al. ................ | 324/220 |
| 3,612,987 | A * | 10/1971 | Placke et al. ................ | 324/242 |
| 3,885,504 | A | 5/1975 | Baermann | |
| 3,940,689 | A * | 2/1976 | Johnson, Jr. ................ | 324/221 |
| 5,359,939 | A * | 11/1994 | Watt ............................ | 104/138.2 |
| 6,232,773 | B1 * | 5/2001 | Jacobs et al. ................ | 324/220 |
| 6,847,207 | B1 * | 1/2005 | Veach et al. ................. | 324/220 |
| 7,784,368 | B2 * | 8/2010 | Gibson et al. ............... | 73/865.8 |

FOREIGN PATENT DOCUMENTS

| | | |
|---|---|---|
| CN | 101291099 A | 4/2007 |
| GB | 2086051 A | 5/1982 |
| GB | 2368399 A | 5/2002 |
| JP | 2005045984 A | 2/2005 |
| JP | 2007110822 A | 10/2005 |
| JP | 2007014110 A | 1/2007 |
| WO | 2006048290 A1 | 5/2006 |

OTHER PUBLICATIONS

GB Office Action dated Sep. 4, 2012 from corresponding Application No. GB0907885.8.

* cited by examiner

*Primary Examiner* — Thomas Valone
(74) *Attorney, Agent, or Firm* — Global Patent Operation (57) ABSTRACT

A magnetizer for a pipeline inspection tool. The magnetizer comprises a ferromagnetic base member, a pair of driving magnets mounted at spatially separate locations on the base member and a flux enhancing magnet mounted on the base member adjacent to one or both of the driving magnets. The directions of magnetization of the pair of driving magnets extend in opposite senses to each other, towards and away from the base member respectively to create a magnetic circuit that includes a flux path between the driving magnets which passes through the base member. The flux enhancing magnet has a direction of magnetization substantially aligned with the direction of magnetic flux on the flux path, the flux enhancing magnet being magnetically coupled to the adjacent driving magnets to drive flux around the magnetic circuit and thereby enhance the magnitude of a magnetic field exhibited by the magnetic circuit outside the magnetizer.

20 Claims, 8 Drawing Sheets

MAGNETISING ASSEMBLY

CROSS-REFERENCE TO RELATED APPLICATION

This application claims priority under 35 U.S.C. §119(a)-(d) or (f) to prior-filed, co-pending British application number 0907885.8, filed on May 7, 2009, which is hereby incorporated by reference in its entirety.

BACKGROUND OF THE INVENTION

1. Field of Invention

The invention relates to a magnetiser for a pipeline inspection tool.

2. Description of Related Art

Pipelines carrying liquid or gaseous products can be inspected automatically from the inside using devices known as intelligent pigs. These devices are usually propelled down the pipe under the flow of product in the pipeline, and utilise magnetic, ultrasonic or other non-destructive techniques to inspect the condition of the pipe wall.

For magnetic methods of inspection, known as the MFL (Magnetic Flux Leakage) technique, the pig has permanent magnets defining first and second pole pieces, which are positioned adjacent the inner wall of the pipe. Those magnets generate magnetic fields which magnetise the wall of the pipe. The MFL technique operates on the principle that an unusual feature in the pipe wall (such as a defect, weld bead or wall thickness change) will disrupt any magnetic flux applied therein, and this disruption (or leakage) may be detected, e.g. by sensors provided between the magnetic poles that detect the magnetic flux density at the internal surface of the pipe. As the pipeline pig is driven along the pipe, the location of the pole pieces, and the sensors, moves along the pipe enabling the internal surface of the pipe to be inspected.

Figure 1:
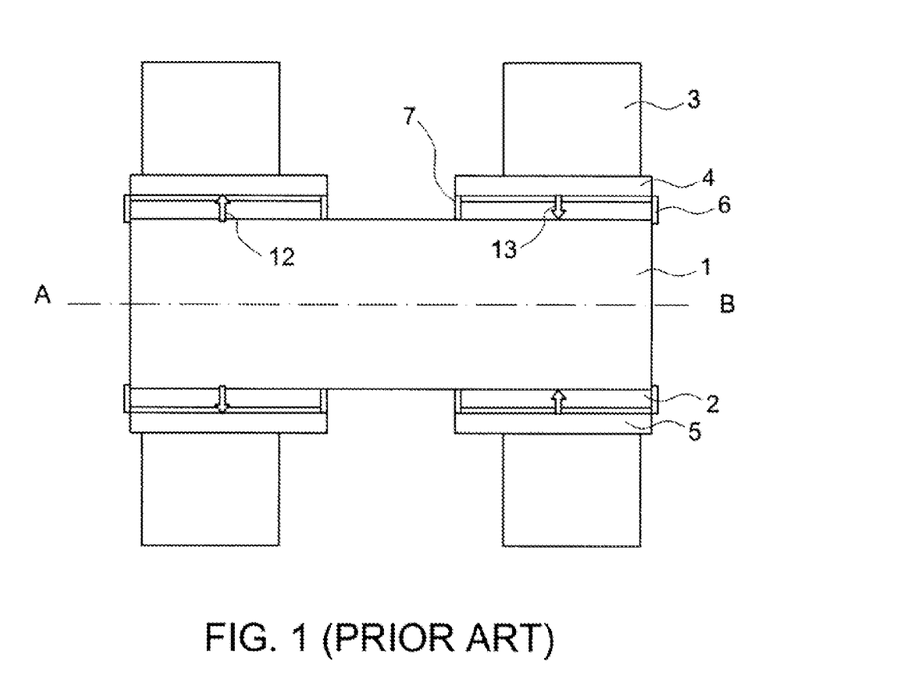
FIG. 1 is a schematic cross-section view through a conventional central body-type magnetiser for an in-line pipe inspection tool, and is discussed above.

FIG. 1 shows a schematic representation of a magnetising assembly 100 for a conventional MFL inspection device. The assembly 100 comprises a central body 1 of mild steel or other ferromagnetic material extending in an axial direction, with radially magnetised magnets 2 fixed around each end to form an annulus. The polarisations, or directions of magnetisation (DOM), of the magnets at each end are opposite to each other, as indicated by respective arrows 12, 13. When the device is inserted into a pipe, ferromagnetic flux couplers 3 couple the flux from the magnets 2 to the pipe wall. The flux couplers 3 may be flexible or semi-rigid, e.g. mild steel bristles. They may provide suspension for the device, e.g. to maintain centrality in the pipe. A ferromagnetic mounting plate or ring 4 allows for easy replacement of the flux couplers 3. The magnets 2 are each protected by steel plates 5, 6 and 7, which form an enclosure to provide protection for the magnets. To allow magnetic coupling between the magnet 2 and the mounting plate 4, the top plate 5 is made from a ferromagnetic material, and to prevent shorting of the magnet 2, the side plates 6 and 7 are made from non-magnetic material.

Figure 2:
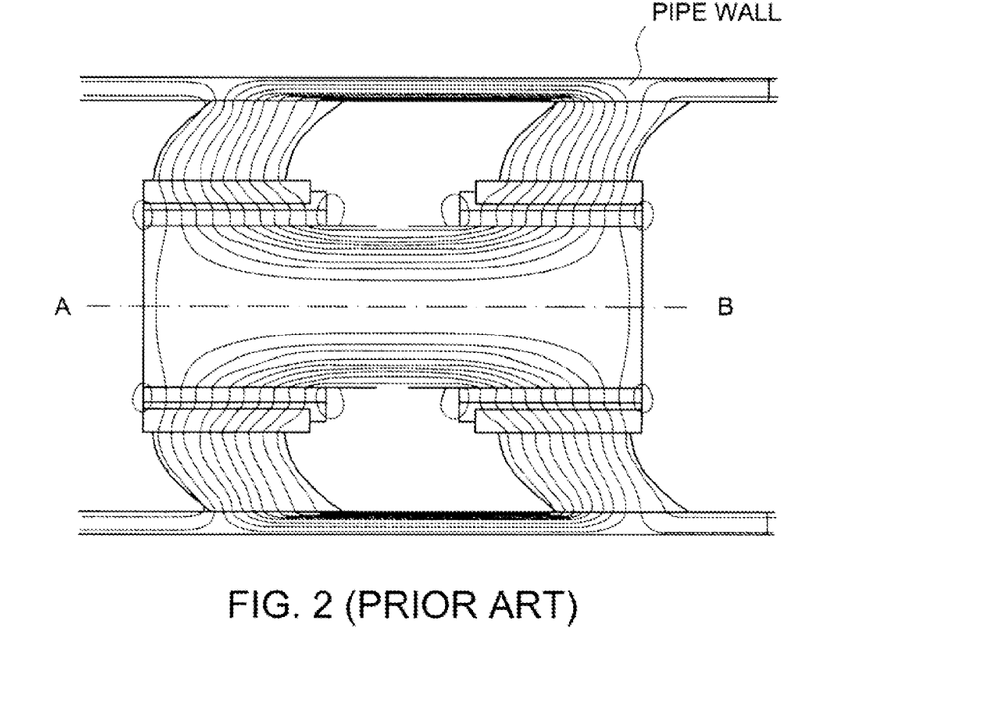
FIG. 2 is a contour plot of the magnetic potential for the magnetiser shown in FIG. 1 when it is inserted inside a pipe, and is also discussed above.

The arrangement shown in FIG. 1 is rotationally symmetric about the body's axis A-B to impart a uniform axial (along the pipe) magnetisation in the pipe wall, permitting inspection by the MFL method. FIG. 2 shows a typical contour plot of lines of magnetic potential from such an arrangement inside a pipe. Here it can be seen that a magnetic flux circuit is generated, whose path flows between the magnets 2 through the pipe wall and central body 1. The central body 1 is often referred to as the return path, because of its role in providing a return route for the magnetic flux circuit between the magnets.

In one example of an inspection device, a circular array of sensors (not shown) would be mounted on the body between the annular magnets in contact with the pipe wall. In the presence of a defect some of the magnetic flux leaks out of the pipe wall and is detected by one or several of the sensors.

An example of the above described scheme is disclosed in U.S. Pat. No. 4,447,777. Other examples, which may be used where the pipeline is straight, with gentle or no bends, the magnets may be shaped, and even non-contacting with the pipe wall (see e.g. U.S. Pat. No. 6,198,277).

The arrangement shown in FIG. 1 is just one possible example of the MFL technique. In another example, the central body may be divided into axially extending segments and mounted off a central suspension mechanism. This obviates the need for the flexible flux couplers of the previous example, allowing shorter, less flexible members to be used to provide the magnetic coupling instead. Examples of such arrangements can be found in U.S. Pat. No. 4,105,972, U.S. Pat. No. 4,310,796, U.S. Pat. No. 5,864,232 and U.S. Pat. No. 6,762,602. All these examples rely on a magnetising assembly having oppositely polarised magnets mounted on both ends of a ferromagnetic magnet bar or return path.

In addition to MFL inspection using an axial magnetic field, transverse field inspection can be achieved by magnetising the pipe wall in the circumferential (around the pipe) direction.

At its most general, the present invention proposes mounting an additional permanent magnet on a magnetising assembly for an in-line pipe inspection tool to enhance (e.g. increase the density of) the magnetic flux in the pipe wall compared with conventional tools of the same size. An increased flux density may permit the tool to perform reliable inspection of thicker pipe walls, smaller pipe diameters and multi-diameter pipeline networks.

BRIEF SUMMARY OF THE INVENTION

According to the invention, there may be provided a magnetiser for an in-line pipe inspection tool, the magnetiser comprising: a ferromagnetic base member; a pair of driving magnets mounted at spatially separate locations on the base member, the directions of magnetisation of the magnets extending in opposite senses to each other, towards and away from the base member respectively, to create a magnetic circuit that includes a flux path between the driving magnets which passes through the base member; and a flux enhancing magnet mounted on the base member adjacent to one or both of the driving magnets and having a direction of magnetisation substantially aligned with the direction of magnetic flux on the flux path, the flux enhancing magnet being magnetically coupled to the adjacent driving magnet(s) to drive flux around the magnetic circuit.

The magnetic coupling between the flux enhancing magnet and driving magnet preferably occurs at a location on the surface of the base member where magnetic isolation was considered necessary in conventional magnetising assemblies for pipeline inspection tools to avoid shorting the magnetic circuit. Somewhat counterintuitively, it has been found that including a magnet at this point actually increases flux in the circuit where it exists outside the magnetiser. Thus, the flux enhancing magnet may be configured to enhance the magnitude of a magnetic field exhibited by the magnetic circuit outside the magnetiser, i.e. to provide a substantial increase in magnetisation performance of the magnetiser.

For example, finite element modelling (FEM) and practical examples demonstrate that using the arrangement defined above can increase the magnetic field in the pipe wall by between 50 and 200% compared with a magnetiser without the flux enhancing magnet. The actual magnitude of the increase may depend on the geometry and the pipe wall thickness.

Herein the term "ferromagnetic" is used to describe materials capable of exhibiting a magnetic polarisation, i.e. material which may contribute to a magnetic flux circuit. One example of a ferromagnetic material may be mild steel. The term "magnet" is used herein to describe permanently magnetised material, i.e. material exhibiting magnetic polarisation in the absence of an external field.

The driving magnets may be mounted on the base member to project away therefrom in the direction of their magnetisations. The term "spatially separate" means that the driving magnets are located physically remotely from each other on the base member. The space between the magnets may house sensors for the in-line pipe inspection tool.

The magnetiser may include a pair of outwardly extending flux couplers, each flux coupler being mounted on a respective driving magnet and being arranged to engage a pipe wall to couple magnetic flux from its respective magnet into the pipe wall. The flux couplers may be flexible, e.g. semi-rigid. This may be useful to accommodate changes in the shape or curvature of the pipe if the magnetiser is fixed relative to the inspection tool. The flux couplers may be ferromagnetic, e.g. mild steel, bristles.

To optimise the flux enhancing effect, the interface (i.e. surface boundary) between the driving magnet and the base member may be aligned with the interface between the flux enhancing magnet and the base member in the region of magnetic coupling between the flux enhancing magnet and its adjacent driving magnet(s).

The flux enhancing magnet may be mounted between the driving magnets and magnetically coupled to both the driving magnets. In other words, the flux enhancing magnet may be mounted within the magnetic circuit.

The flux enhancing magnet may be modular, i.e. it may comprise a pair of spatially separated magnetic modules, each magnetic module being mounted within the magnetic circuit adjacent a respective driving magnet. The base member may include a link portion located between the modules to provide a optimal path for flux to pass therebetween.

The flux coupling magnet may cover all of the outer surface of the base member between the driving magnets, e.g. to prevent or minimise flux leakage from the base member.

The magnetiser may have a recess formed in the outer surface that extends between the driving magnets, the recess being setback from the outer surface of the flux enhancing magnet in the region of magnetic coupling between the flux enhancing magnet and its adjacent driving magnet(s). The recess may be arranged to accommodate one or more sensors for the in-line pipe inspection tool. The recess is located in the above-described manner to minimise its effect on the function of the flux enhancing magnet. The recess may exist between a pair of magnetic modules, where the flux enhancing magnet is modular. For example, the recess may be formed in the link portion of the base member. Preferably, the bottom of the recess is located to ensure that the modules are linked by a piece of ferromagnetic material that extends in their direction of magnetisation. In other embodiments, the recess may be formed in the flux enhancing magnet itself, e.g. where this magnet extends across the outer surface of the base member between the driving magnets.

One or both of the driving magnets may be made up of two or more subcomponents. For example, one or both of the driving magnets may comprise an interface section mounted on the base member at the region of magnetic coupling with the flux enhancing magnet, and a main section mounted on the base member next to the interface section, the interface section having a higher coercivity than the main section. The higher coercivity at the interface with the flux enhancing magnet may minimise flux leakage in this region by preventing, reducing or minimising demagnetisation of the driving magnet due to the proximity of the flux enhancing magnet's orthogonal field. Each driving magnet may be mounted in a housing on the base member, e.g. to provide structural strength to the assembly that may not be available using the magnets alone. Similarly, the flux enhancing magnet may be mounted on the base member in a housing. To ensure magnetic coupling between the driving magnets and the flux enhancing magnet, each housing may comprise ferromagnetic material at the boundaries between those magnets. The housing may include non-magnetic material elsewhere, e.g. to prevent shorting of the magnetic circuit.

The shape of the driving magnets may be selected to enhance further the magnetic flux. For example, the thickness in the direction of magnetisation of one or both of the driving magnets may increase with distance away from the flux enhancing magnet. This may increase the magneto-motive force of the assembly and provide an additional contribution to the field generated by the magnetic circuit outside the assembly. The increase in thickness of the driving magnet(s) may be accommodated by a decrease in thickness of the base member. In other words the base member may taper towards the ends of the assembly.

The invention set out above may be applicable to the conventional longitudinal central body and segmented body arrangements. For example, the base member may be an elongate body having a body axis (e.g. central axis) and being arranged to travel in the direction of its axis along a pipeline, the directions of magnetisation of the driving magnets extending radially with respect to the body axis and the direction of magnetisation of the flux enhancing magnet being aligned with the body axis.

For the central body arrangement, the body may be arranged to be coaxial with the pipeline and the driving magnets and flux enhancing magnet may exhibit rotational symmetry about the body axis. In one embodiment, the driving magnets and flux enhancing magnet may be annular elements arranged on the body.

For the segmented body arrangement, the base member may comprise a plurality of circumferentially separate segments mounted around a magnetiser axis and extending parallel thereto. Each base member may have mounted thereon a pair of driving magnets and flux enhancing magnet as set out above. The arrangement of the magnetic elements preferably has rotational symmetry about the magnetiser axis. This may facilitate generating a uniform field in the pipe wall. Each segment may be mounted via a suspension mechanism on a tool body.

The invention may also be applicable to the conventional transverse field arrangements. In other words, whilst the longitudinal arrangements may spatially separate the driving magnets in a direction along the body axis, in the transverse arrangement the driving magnets may be spatially separated in a direction around the circumference of the body, with the direction of magnetisation in the flux enhancing magnet extending transversely with respect to the body axis.

In another aspect, the invention may provide an in-line pipe inspection tool for travelling along a pipeline axis, the tool comprising a magnetiser having: a ferromagnetic base member; a pair of driving magnets mounted at spatially separate locations on the base member, the directions of magnetisation of the magnets extending radially with respect to the pipeline axis and in opposite senses to each other to create a magnetic circuit that includes a flux path between the driving magnets which passes through the base member, and a flux enhancing magnet mounted on the base member adjacent to one or both of the driving magnets and having a direction of magnetisation substantially aligned with the direction of magnetic flux on the flux path, the flux enhancing magnet being magnetically coupled to the adjacent driving magnet(s) to drive flux around the magnetic circuit.

The magnetiser may include any of the features discussed above. For example, the magnetiser may include a pair of radially extending flux couplers, each flux coupler being mounted on a respective driving magnet and being arranged to engage a pipe wall to couple magnetic flux from its respective magnet into the pipe wall.

The in-line pipe inspection tool may be of the central body type, e.g. where the base member comprises a body extending parallel to the pipeline axis and the driving magnets and flux enhancing magnets are arranged as annular bodies on the base member. Alternatively, the in-line pipe inspection tool may be of the segmented body type, e.g. where the magnetiser is arranged as a plurality of circumferentially separate segments mounted around the pipeline axis and extending parallel thereto. The in-line pipe inspection tool may be of the transverse type, e.g. where the driving magnets may be spatially separated in a direction around the circumference of the body and the direction of magnetisation in the flux enhancing magnet extends transversely with respect to the body axis.

BRIEF DESCRIPTION OF THE DRAWINGS

Examples of the invention are discussed below with reference to the accompanying drawings, in which.

DETAILED DESCRIPTION OF THE INVENTION

Figure 3:
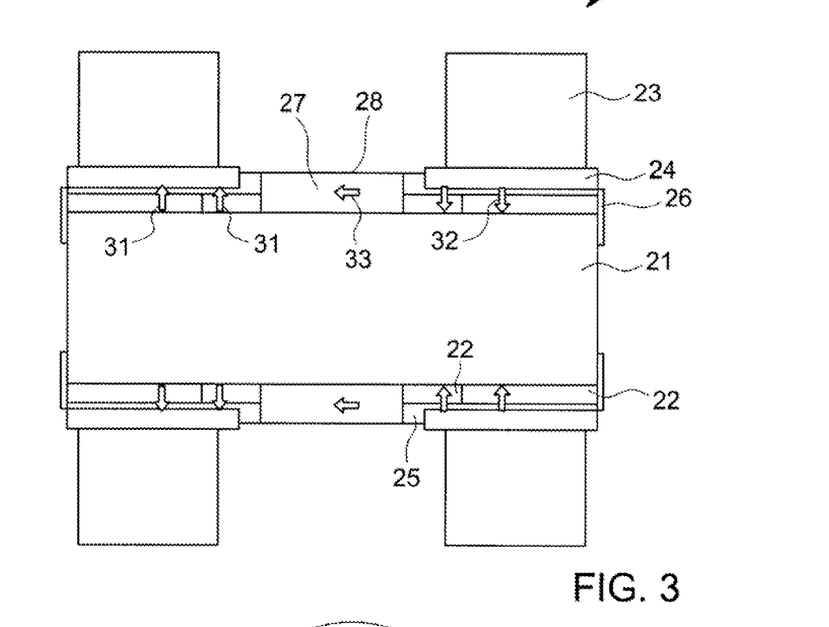
FIG. 3 a schematic cross-section view through a central body-type magnetiser for an in-line pipe inspection tool that is a first embodiment of the invention.

FIG. 3 shows a first example of a magnetiser 20 that embodies the invention. This embodiment is a central body-type arrangement similar to the conventional magnetising assembly shown in FIG. 1. The magnetiser 20 comprises a central body (i.e. base member) 21 of ferromagnetic material (e.g. mild steel), with annular driving magnets 22 fixed around each end. The directions of magnetisation (DOM) of the magnets 22 at each end are opposite to each other, as indicated by respective arrows 31, 32. Each driving magnet is enclosed in a housing comprising top plate 25 and end plate 26. The housing provides protection for the driving magnet and structural support for the elements that are mounted on each magnet. A ferromagnetic mounting plate 24 is fixed on each driving magnet 22 to receive a respective ferromagnetic flux coupler 23, e.g. comprising flexible mild steel bristles. The flux couplers 23 are arranged to couple the flux from the driving magnets 22 into a pipe wall and provide suspension for the device in the pipe. The top plate 25 is ferromagnetic to permit the magnetic field from its driving magnet to be transferred through to the flux coupler 23. To prevent shorting of the magnet 22, the side plate 26 is made of a non-magnetic material.

The magnetiser functions in the same way as described above with respect to FIG. 1. The main difference is the presence of an additional annular magnet 27 mounted on the central body 21 between the annular driving magnets 22 and magnetised in the axial direction (parallel to the axis of the central body 21, as indicated by arrow 33). This additional magnet, hereinafter referred to as a flux enhancing magnet, provides an additional source of magnetic flux in the circuit. This additional tube-shaped magnet 27 may appear counterintuitive because one might expect it to be short circuited by the central mild steel body 21. However, finite element modelling of the magnetic potential shows that the presence of the driving magnets 22 at each end of the flux enhancing magnet 27 act to inhibit this effect and prevent the flux turning back on itself down the central body 21. The flux enhancing magnet 27 not only provides additional magnetic flux in the magnetic circuit also helps to block flux leaking back onto the body due from the driving magnets 22. In conventional arrangements, this leakage is coupled through the air; in the invention it is blocked by locating the flux enhancing magnet 27 such that it covers the edge of the driving magnet. In other words, the edge of the driving magnets extending parallel to their direction of magnetisation are bounded by the flux enhancing magnet. Overall, the new arrangement provides an increase in the magnet flux output of the device.

Each of the driving magnets 22 has two component pieces. As there are high demagnetising fields close to the inside corner of the flux enhancing magnet 27 at the junction with the central body 21, the driving magnets may comprise an interface portion at this position that has a higher coercivity that a main portion located under the flux couplers. The higher coercivity interface portion may reduce or overcome any demagnetisation losses. The two piece configuration may provide an optimised balance between magnetic strength (i.e. maximising the flux density available to drive the magnetic circuit) and resistance to demagnetisation, which can indirectly influence magnetic strength by retaining tighter control over the directions of magnetisation. The higher coercivity material (which may not be as magnetically strong as the main portion) may act as a buffer to absorb any demagnetising effects without being demagnetised itself. In other embodiment, a single material may be used which exhibits both the desired magnetic strength and resistance to demagnetisation.

The flux enhancing magnet 27 is covered by a thin protective sheath 28. The sheath is made of a non-magnetic material.

The sheath may protect and magnetically isolate the magnet 27 from sensing components (not shown) that may be mounted thereon.

As the permanent magnets 22, 27 may generally be made from brittle material, they may not be suitable for use as structural components, hence the presence of the housing and protective sheath. The material for these structures must be carefully selected to ensure good magnetic connectivity between the magnets and the pipe wall couplers, but must be made of non-magnetic material along the sides to prevent magnetic shorting.

Figure 4:
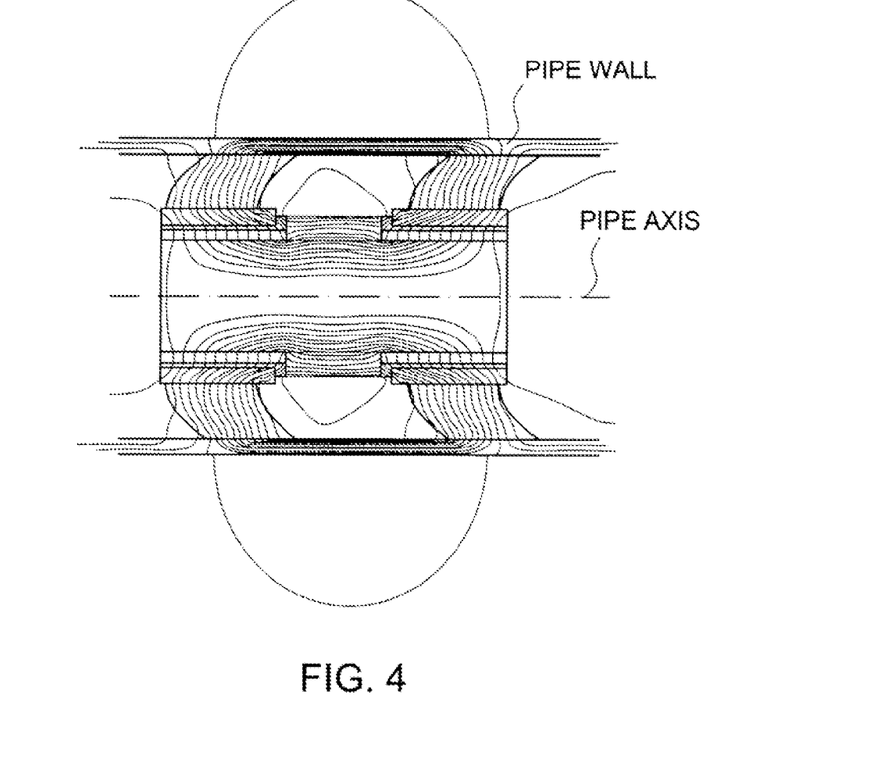
FIG. 4 is a contour plot of the magnetic potential for the magnetiser shown in FIG. 3 when it is inserted inside a pipe.

FIG. 4 shows a contour plot of lines of magnetic potential for the first embodiment inside a pipe. When compared with the plot shown in FIG. 2, it may be seen that the presence of the flux enhancing magnet acts to supplement and push the flux through the adjacent steel components.

Figure 5:
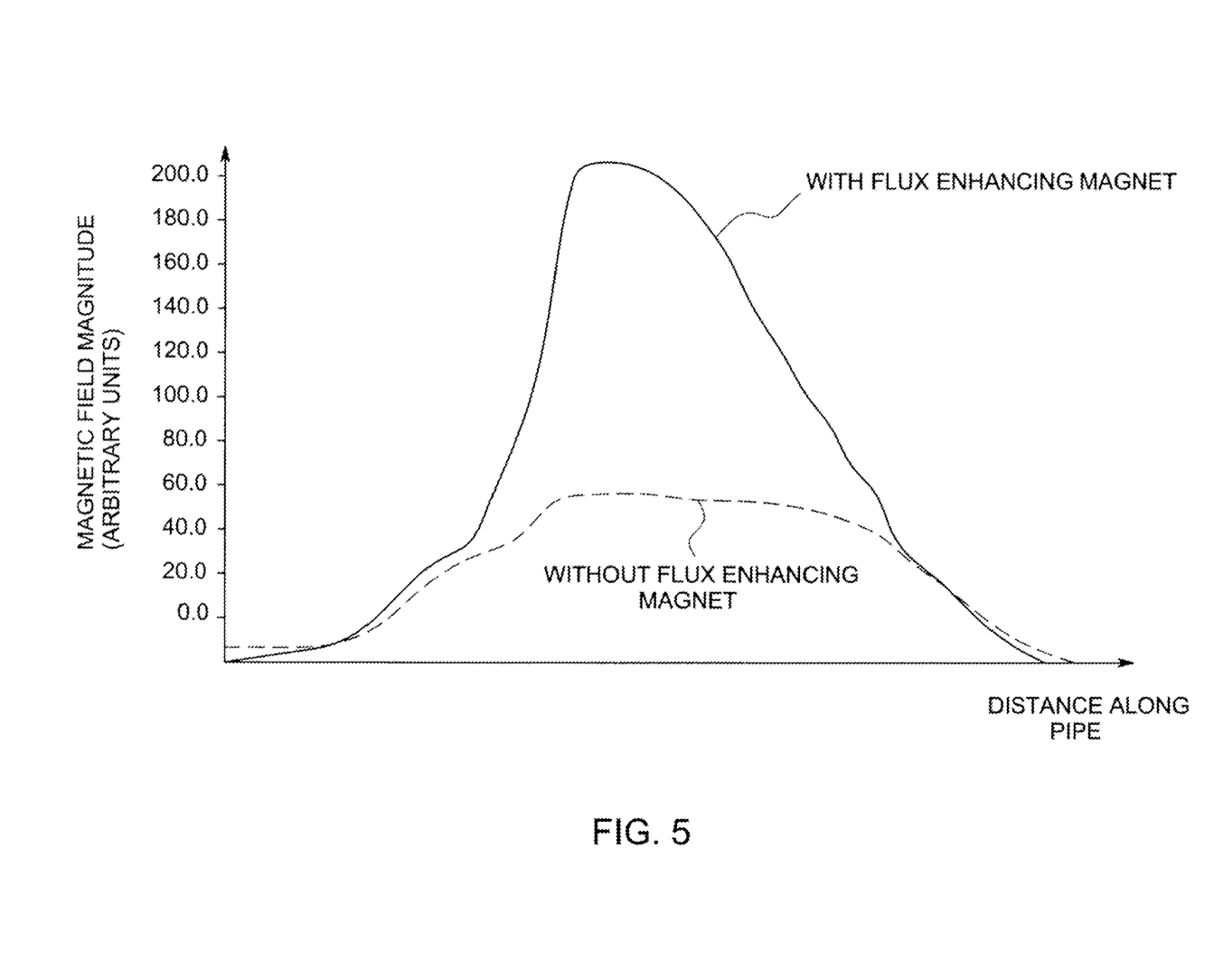
FIG. 5 is a graphical comparison of axial pipe wall profiles for a magnetiser with and without the flux enhancing magnet.

The magnetic potential plot shown in FIG. 4 serves to show the flux lines or distribution of magnetic potential. FIG. 5 illustrates quantitatively the superiority of the invention. FIG. 5 is a graphical representation of the axial component of field in the pipe wall for a conventional magnetiser without a flux enhancing magnet (dotted line) and a magnetiser with a flux enhancing magnet according to the invention (solid line). The vertical axis represents field magnitude (in arbitrary units) and the horizontal axis represents the distance along the pipe. A peak in the field magnitude occurs between the flux couplers, where MFL sensors may be located. FIG. 5 shows that in the peak region, the field is increased by the order of 200%. Such an improvement in field allows increased confidence of pipe wall saturation and more confident and accurate inspection. The two schemes being compared have the same axial length, same central body diameters, and same outer diameter across the radial magnets. The only difference is the inclusion of the blocking magnet.

The principles of the invention discussed above can be applied to other embodiments, which are discussed below.

Figure 6:
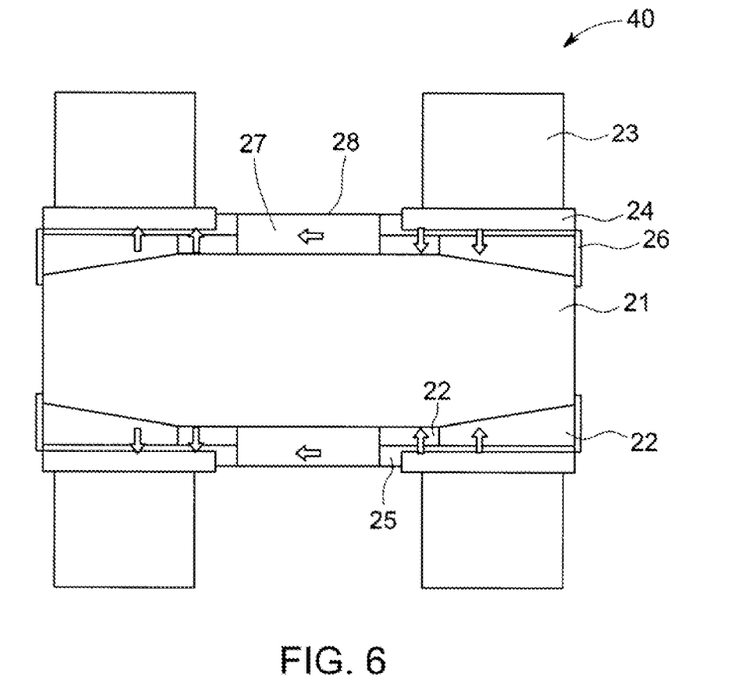
FIG. 6 is a schematic cross-section view through a central body-type magnetiser for an in-line pipe inspection tool that is a second embodiment of the invention.

FIG. 6 is cross-section view through a central body-type magnetiser 40 that is a second embodiment of the invention. Components in FIG. 6 which perform the same function as those in FIG. 3 are given the same reference numbers. In this embodiment, the central body 21 tapers, i.e. exhibits a conical shape, underneath the driving magnets 22. The driving magnets 22 (specifically the main part of each driving magnet) are fitted to the tapered body. As a result, the radial thickness of the driving magnets increases towards their respective end plates 26. The purpose of this thickening is to increase the magneto-motive force of the assembly in this region and contribute to an additional increase in the pipe wall field.

Figure 7:
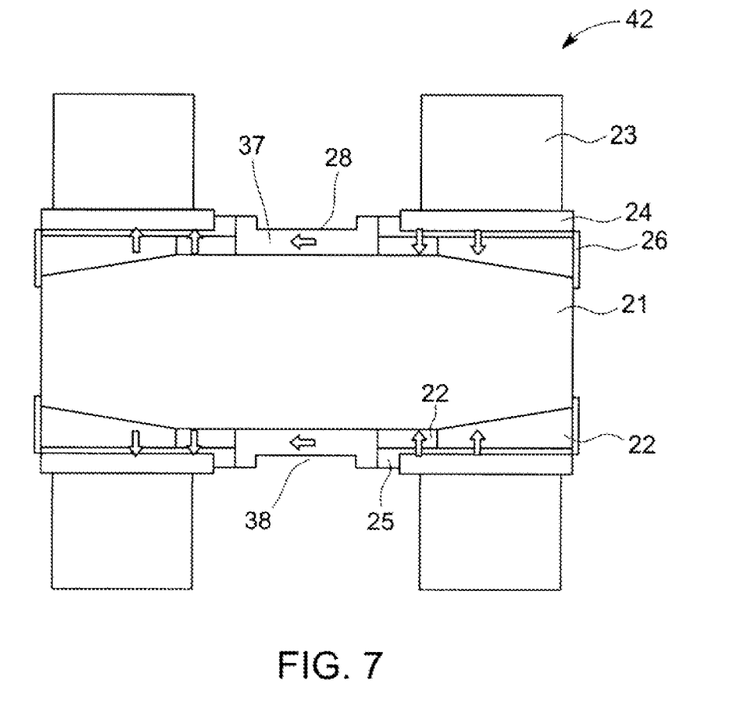
FIG. 7 is a schematic cross-section view through a central body-type magnetiser for an in-line pipe inspection tool that is a third embodiment of the invention.

FIG. 7 is cross-section view through a central body-type magnetiser 42 that is a third embodiment of the invention. Components in FIG. 7 which perform the same function as those in FIG. 3 are given the same reference numbers. In this embodiment, the flux enhancing magnet 37 includes a recess 38 formed in its outer surface. In other words, the outer diameter of the flux enhancing magnet 37 is reduced over its central section. The purpose of this thinning may be to accommodate sensors and/or other inspection electronics on the tool. FEM may be used to find a configuration where the recess is of a suitable size for receiving sensors or the like yet the flux enhancing magnet still confers an adequate increase in field strength.

Figure 8:
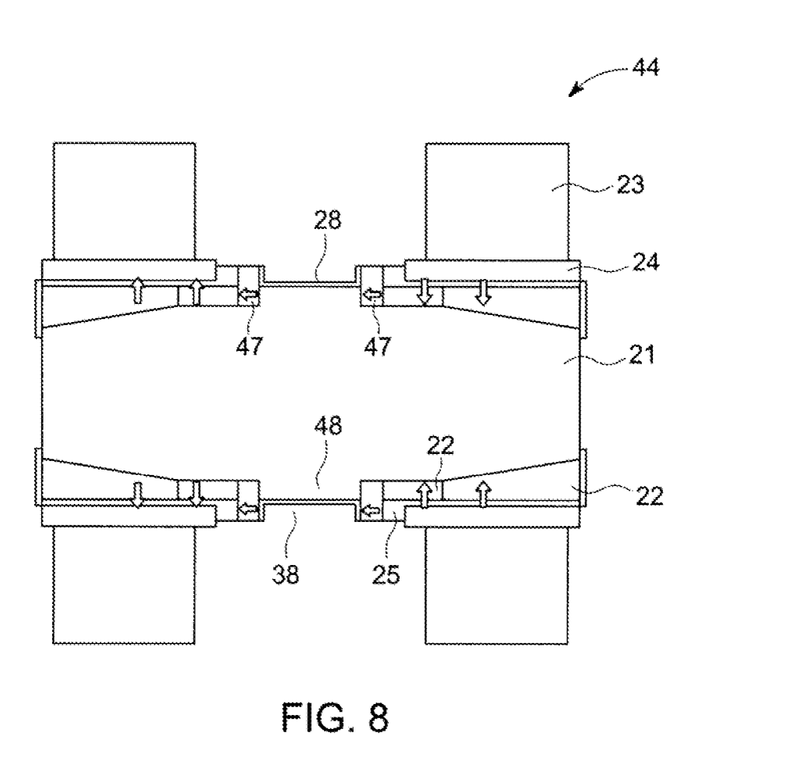
FIG. 8 is a schematic cross-section view through a central body-type magnetiser for an in-line pipe inspection tool that is a fourth embodiment of the invention.

FIG. 8 is cross-section view through another central body-type magnetiser 44 that is a fourth embodiment of the invention. Components in FIG. 8 which perform the same function as those in FIG. 3 are given the same reference numbers. In this embodiment, the flux enhancing magnet 47 comprises two spatially separated magnetic modules. Each module is located within the magnetic circuit in a region immediately adjacent to a respective driving magnet 22. The edges of the driving magnets 22 are thus still covered by the flux enhancing magnet 47 to prevent flux leakage. To facilitate magnetic communication between the modules, the central body 21 may include a thickened band between the modules that acts as a link portion providing magnetic communication therebetween. The outer surface of the link portion may be set back from the outer surface of the modules to provide a recess 38 for the same purpose as discussed above. FEM may be used to find a configuration (specifically an axial length) for the modules which provides a magneto-motive force to confer an adequate increase in field strength.

Figure 9:
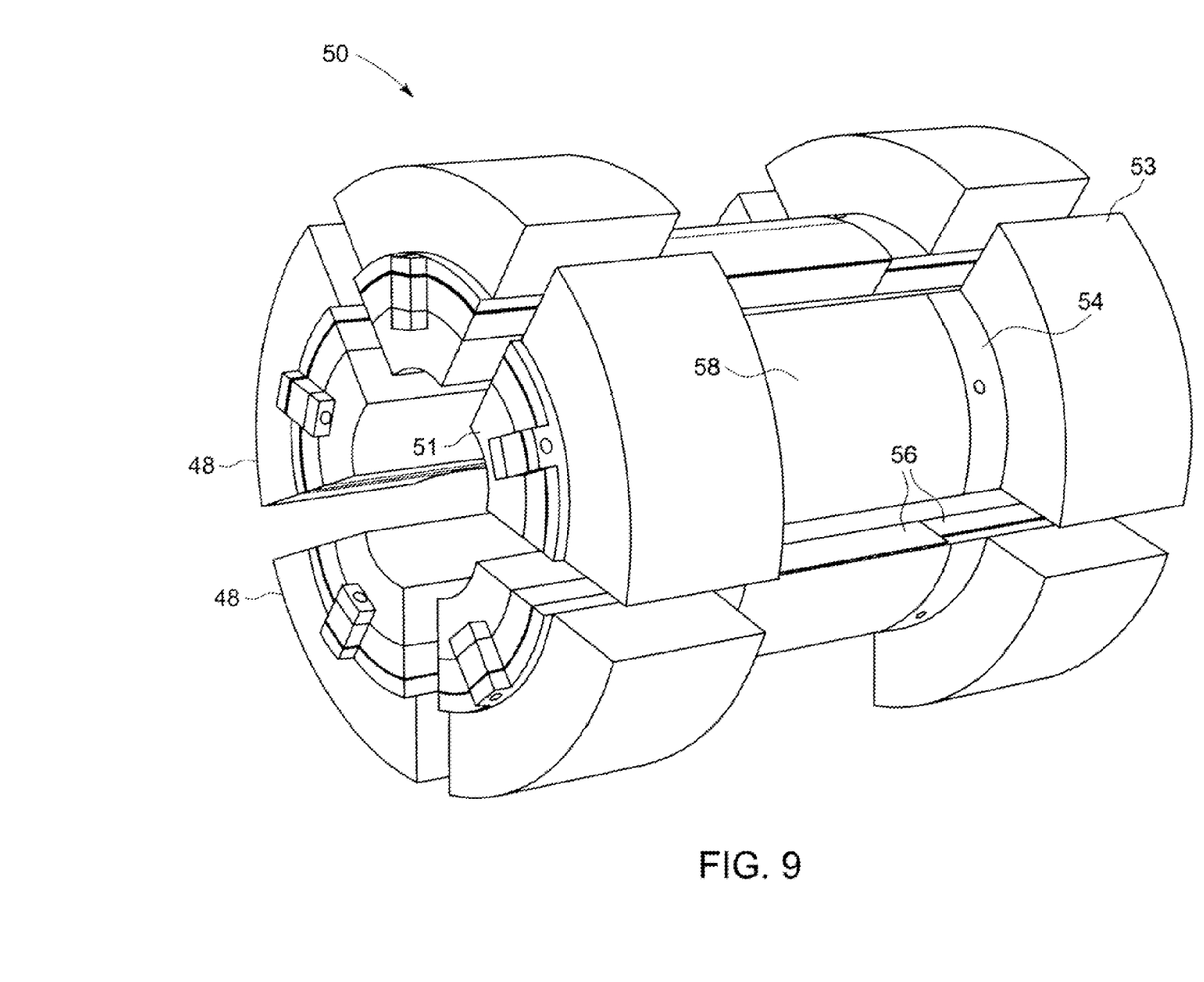
FIG. 9 is a perspective view of a segmented body-type magnetiser for an in-line inspection tool that is a fifth embodiment of the invention.

The embodiments described with respect to FIGS. 3, 6, 7 and 8 are based on a central body design. However, the same principles may be applied to a segmented magnetiser. FIG. 9 shows a perspective view of a segmented magnetiser 50 that is another embodiment of the invention. In the segmented arrangement, the cylindrical symmetry of the central body arrangement is interrupted because the body is divided into a plurality of discrete segments 48. The magnetiser 50 may still exhibit rotational symmetry about a tool axis around which the segments 48 are arranged. Each segment 48 comprises a ferromagnetic base member 51 (e.g. a backing bar) extending parallel to the tool axis. To approximate to the central body arrangement, each segment 48 has a pair of driving magnets 52 (not visible in FIG. 9) mounted at each end of the base member 51 and having a direction magnetisation extending radially with respect to the tool axis and in opposite senses to each other. Similar to the embodiments discussed above, a ferromagnetic mounting plate 54 is fixed on each driving magnet 52 (or on a structural support shell (not shown) enclosing the magnet. A flux coupler 53 is mounted on each mounting plate. A protective coating 58 covers the flux enhancing magnet and/or base member 51 in the region between the flux couplers 53.

Figure 10:
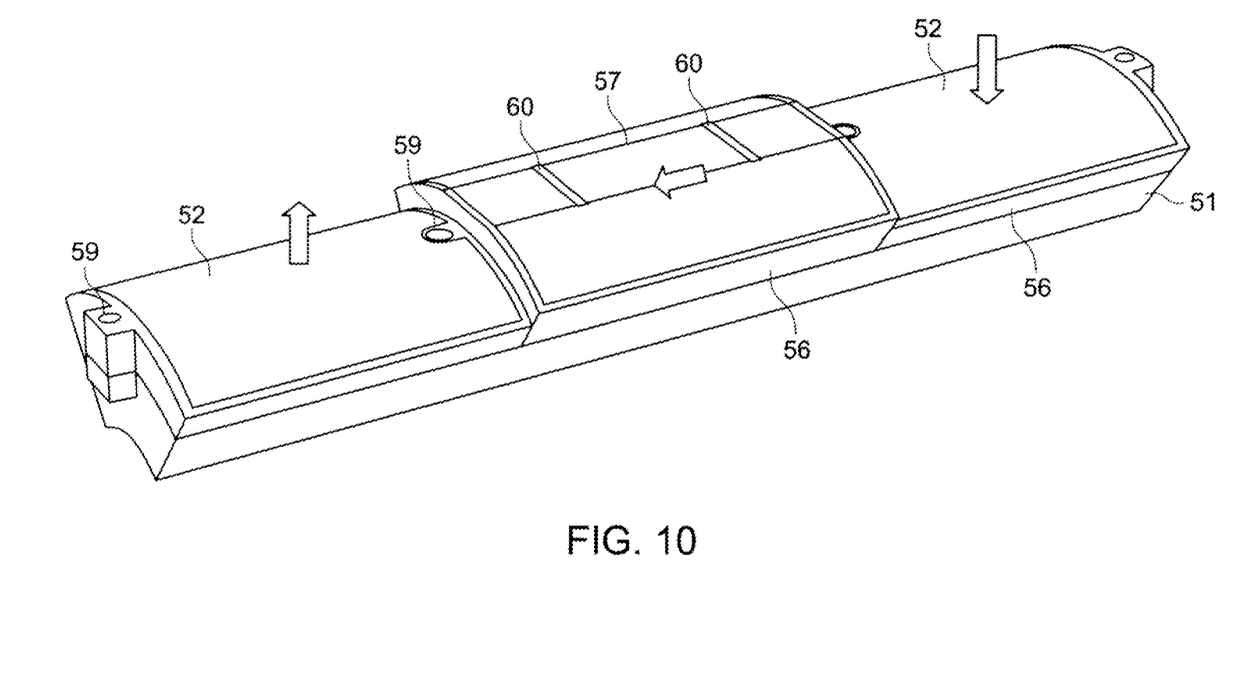
FIG. 10 is a perspective view of a segment from the magnetiser shown in FIG. 9.

The three-dimensional perspective view in FIG. 9 conceals some details of the embodiment, so a single magnetiser segment with the flux couplers 53 removed is shown in FIG. 10. Here the driving magnets 52 are shown embedded within structural enclosures 56, mounted on the base member 51, a single backing bar. A flux enhancing magnet 57 is mounted between the driving magnets 52, also embedded in an enclosure that provides structural support, e.g. at the axial ends and along the sides of the segment.

The assembly illustrated in FIG. 10 also shows mounting holes 59 formed in the enclosure 56 and slots 60 formed within the body of the flux enhancing magnet that are used to attach the segment to the tool and to other components, such as flux couplers, sensors and external electronics. The robustness of the magnetic circuit is demonstrated in this segmented embodiment by the fact that the interruptions to the flux path, e.g. caused by physical separation of the magnets by the thickness of the enclosure walls, do not substantially affect the operation of or benefits afforded by the invention.

Figure 11:
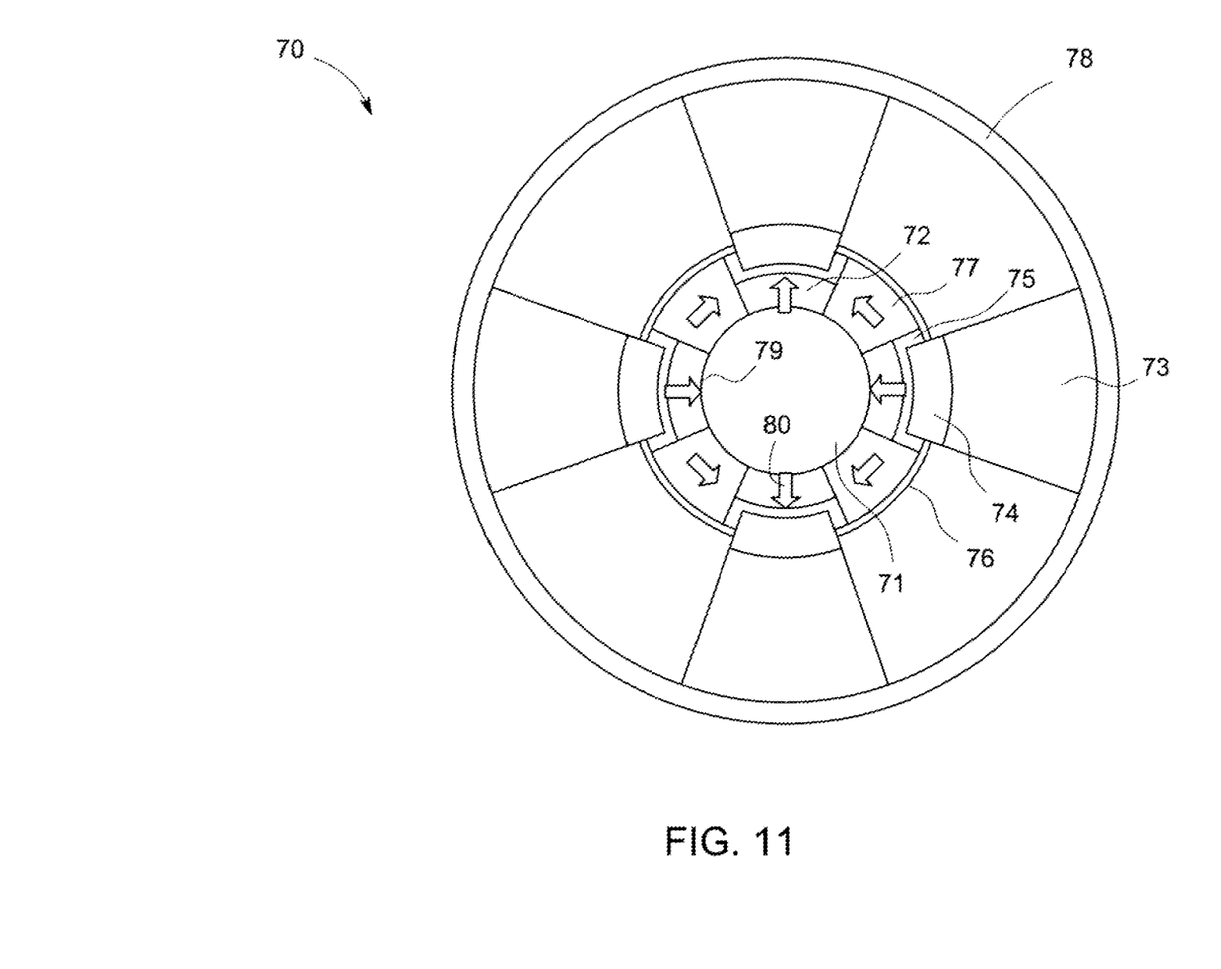
FIG. 11 is a schematic cross-section view through a transverse-type magnetiser for an in-line pipe inspection tool that is a sixth embodiment of the invention.

FIG. 11 shows the invention applied to a transverse type magnetiser, i.e. in which the pipe wall is magnetised in a circumferential direction relative to a tool axis as opposed to the axial magnetic field imparted by the preceding embodiments. FIG. 11 is a cross-sectional view through a transverse-type magnetiser 70 located inside a pipe wall 78.

In this embodiment, the transverse-type magnetiser 70 incorporates a quadrupole arrangement, but the same principles are applicable to a dipole arrangement or any other multi-pole arrangement.

The transverse-type magnetiser 70 has a central body (base member) 71; the view is FIG. 11 is down the body axis. Four driving magnets 72 are mounted on the body 71 at spatially separated locations. The driving magnets 72 are radially polarised, with the adjacent magnets polarised in the opposite sense to each other, as indicated by respective arrows 79, 80. A top plate 75 is fixed to each driving magnet to protect it and provide structural support for a ferromagnetic mounting plate 74, on which is mounted a flexible flux coupler 73. These elements have corresponding functions to like named parts on the longitudinal arrangements discussed above. A flux enhancing magnet 77 is mounted on the body 71 in between each respective pair of driving magnets 72. Each flux enhancing magnets is polarised in a circumferential sense in the same direction as flux in the body due to the magnetic circuit generated by the driving magnets 72. A protective coating 76 covers the flux enhancing magnets 77 between each pair of adjacent flux couplers 73.

What is claimed is:

1. A magnetiser for an in-line pipe inspection tool, the magnetiser comprising:
    a ferromagnetic base member;
    a pair of driving magnets mounted at spatially separate locations on the base member, the directions of magnetisation of the magnets extending in opposite senses to each other, towards and away from the base member respectively, to create a magnetic circuit that includes a flux path between the driving magnets which passes through the base member; and
    a flux enhancing magnet mounted on the base member adjacent to one or both of the driving magnets and having a direction of magnetisation substantially aligned with the direction of magnetic flux on the flux path, the flux enhancing magnet being magnetically coupled to the adjacent driving magnet(s) to drive flux around the magnetic circuit and thereby enhance the magnitude of a magnetic field exhibited by the magnetic circuit outside the magnetizer;
    wherein a thickness in the direction of magnetisation of one or both of the driving magnets increases with distance away from the flux enhancing magnet.

2. A magnetiser according to claim 1 including a pair of outwardly extending flux couplers, each flux coupler being mounted on a respective driving magnet and being arranged to engage a pipe wall to couple magnetic flux from its respective magnet into the pipe wall.

3. A magnetiser according to claim 2, wherein the flux enhancing magnet is configured to provide an increase in the magnetic field in the pipe wall of between 50 and 200% compared with the magnetic field from the magnetiser without the flux enhancing magnet.

4. A magnetiser according to claim 1, wherein the interface between the driving magnet and the base member is aligned with the interface between the flux enhancing magnet and the base member in the region of magnetic coupling between the flux enhancing magnet and its adjacent driving magnet(s).

5. A magnetiser according to claim 1, wherein the flux, enhancing magnet is mounted between the driving magnets and magnetically coupled to both the driving magnets.

6. A magnetiser according to claim 5, wherein the flux enhancing magnet comprises a pair of spatially separated magnetic modules, each magnetic module being mounted within the magnetic circuit adjacent a respective driving magnet.

7. A magnetiser according to claim 5, wherein the flux enhancing magnet covers all of the outer surface of the base member between the driving magnets.

8. A magnetiser according to claim 1, having a recess formed in the outer surface that extends between the driving magnets, the recess being set back from the outer surface of the flux enhancing magnet in the region of magnetic coupling between the flux enhancing magnet and its adjacent driving magnet(s).

9. A magnetiser according to claim 1, wherein one or both of the driving magnets comprises an interface section mounted on the base member at the region of magnetic coupling with the flux enhancing magnet, and a main section mounted on the base member next to the interface section, the interface section having a higher coercivity than the main section.

10. A magnetiser according to claim 1, wherein the increase in thickness of the driving magnets is accommodated by a decrease in thickness of the base member.

11. A magnetiser according to claim 1, wherein the base member is an elongate body having a central axis and being arranged to travel in the direction of its axis along a pipeline, the directions of magnetisation of the driving magnets extending radially with respect to the body axis.

12. A magnetiser according to claim 11, wherein the body is arranged to be coaxial with the pipeline and the driving magnets and flux enhancing magnets exhibit rotational symmetry about the body axis.

13. A magnetiser according to claim 11, wherein the driving magnets are spatially separated in a direction along the body axis and the direction of magnetisation of the flux enhancing magnet is aligned with the body axis.

14. A magnetiser according to claim 11, wherein the driving magnets are spatially separated in a direction around the perimeter of the body and the direction of magnetisation of the flux enhancing magnet extends transversely to the body axis.

15. An in-line pipe inspection tool for travelling along, a pipeline axis, the tool comprising a magnetiser having:
    a ferromagnetic base member;
    a pair of driving magnets mounted at spatially separate locations on the base member, the directions of magnetisation of the magnets extending radially with respect to the pipeline axis and in opposite senses to each other to create a magnetic circuit that includes a flux path between the driving magnets which passes through the base member; and
    a flux enhancing magnet mounted on the base member adjacent to one or both of the driving magnets and having a direction of magnetisation substantially aligned with the direction of magnetic flux on the flux path, the flux enhancing magnet being magnetically coupled to the adjacent driving magnet(s) to drive flux around the magnetic circuit;
    wherein a thickness in the direction of magnetisation of one or both of the driving magnets increases with distance away from the flux enhancing magnet.

16. An in-line pipe inspection tool according to claim 15, wherein the magnetiser includes a pair of radially extending flux couplers, each flux coupler being mounted on a respective driving magnet and being arranged to engage a pipe wall to couple magnetic flux from its respective magnet into the pipe wall.

17. An in-line pipe inspection tool according to claim 15, wherein the base member comprises a body extending parallel to the pipeline axis and the driving magnets and flux enhancing magnets are arranged as annular bodies on the base member.

18. An in-line pipe inspection tool according to claim 17, wherein the driving magnets are spatially separated in a direction along the pipeline axis and the direction of magnetisation of the flux enhancing magnet is aligned with the pipeline axis.

19. An in-line pipe inspection tool according to claim 15, wherein the magnetiser is arranged as a plurality of circumferentially separate segments mounted around the pipeline axis and extending, parallel thereto.

20. An in-line pipe inspection tool according to claim 19, wherein the driving magnets are spatially separated in a direction around the perimeter of the body and the direction of magnetisation of the flux enhancing magnet extends transversely to the pipeline axis.

* * * * *

UNITED STATES PATENT AND TRADEMARK OFFICE
CERTIFICATE OF CORRECTION

PATENT NO. : 8,487,610 B2  
APPLICATION NO. : 12/772373  
DATED : July 16, 2013  
INVENTOR(S) : Mundell Page 1 of 1

It is certified that error appears in the above-identified patent and that said Letters Patent is hereby corrected as shown below:

In the Specification

In Column 3, Line 48, delete "setback" and insert -- set back --, therefor.

In Column 5, Line 3, delete "base member," and insert -- base member; --, therefor.

In the Claims

In Column 9, Line 55, in Claim 5, delete "flux," and insert -- flux --, therefor.

In Column 10, Line 16, in Claim 11, delete "haying" and insert -- having --, therefor.

In Column 10, Line 33, in Claim 15, delete "along," and insert -- along --, therefor.

In Column 11, Line 4, in Claim 19, delete "extending," and insert -- extending --, therefor.

Signed and Sealed this  
Twelfth Day of November, 2013

Teresa Stanek Rea  
*Deputy Director of the United States Patent and Trademark Office*